United States Patent [19]

Horvath et al.

[11] Patent Number: 5,054,321

[45] Date of Patent: Oct. 8, 1991

[54] METHOD AND APPARATUS FOR MEASURING SURFACE CONTOUR ON PARTS WITH ELEVATED TEMPERATURES

[75] Inventors: Mark S. Horvath, Canton, Mich.; Roy A. Nance, McMurray, Pa.; George H. Cohen, Pittsburgh, Pa.; George Fodor, Pittsburgh, Pa.

[73] Assignee: The United States of America as represented by the United States Department of Energy, Washington, D.C.

[21] Appl. No.: 531,356

[22] Filed: May 31, 1990

[51] Int. Cl.$^5$ .................................... G01N 29/00
[52] U.S. Cl. ................................. 73/597; 73/644
[58] Field of Search ............... 73/644, 597, 620, 627, 73/629

[56] References Cited

U.S. PATENT DOCUMENTS

| | | |
|---|---|---|
| 2,751,783 | 6/1956 | Erdman .................................. 73/644 |
| 3,662,590 | 5/1972 | Shiraiwa ................................ 73/644 |
| 3,898,839 | 8/1975 | White .................................... 73/644 |
| 3,910,104 | 10/1975 | Davies ................................... 73/644 |
| 3,946,599 | 3/1976 | Patt ....................................... 73/644 |
| 4,403,510 | 9/1983 | De Walle .............................. 73/644 |
| 4,483,195 | 11/1984 | Brown et al. ......................... 73/644 |
| 4,507,969 | 4/1985 | Djordjevic ............................ 73/644 |
| 4,526,038 | 7/1985 | Box ....................................... 73/644 |
| 4,530,246 | 7/1985 | Pitman .................................. 73/644 |
| 4,558,598 | 12/1985 | Young ................................... 73/644 |
| 4,726,231 | 2/1988 | Tretout et al. ........................ 73/644 |
| 4,862,748 | 9/1989 | Woodmansee ....................... 73/644 |
| 4,944,186 | 7/1990 | Dorr ...................................... 73/644 |

Primary Examiner—Hezron E. Williams
Assistant Examiner—Rose M. Finley
Attorney, Agent, or Firm—Virginia B. Caress; William R. Moser; Richard E. Constant

[57] ABSTRACT

The invention is directed to a method and apparatus for measuring the surface contour of a test piece, such as the bow of a radioactive fuel rod, which is completely immersed in water. The invention utilizes ultrasonic technology and is capable of measuring surface contours of test pieces which are at a higher temperature than the surrounding water. The presence of a test piece at a higher temperature adversely affects the distance measurements by causing thermal variations in the water near the surface of the test piece. The contour measurements depend upon a constant temperature of the water in the path of the ultrasonic wave to provide a constant acoustical velocity (the measurement is made by the time of flight measurement for an ultrasonic wave). Therefore, any variations of water temperature near the surface will introduce errors degrading the measurement. The present invention overcomes these problems by assuring that the supply of water through which the ultrasonic waves travel is at a predetermined and constant temperature.

10 Claims, 2 Drawing Sheets

METHOD AND APPARATUS FOR MEASURING SURFACE CONTOUR ON PARTS WITH ELEVATED TEMPERATURES

The U.S. Government has rights in this invention pursuant to Contract No. DE-AC11-76PN00014.

BACKGROUND OF THE INVENTION

The present invention relates to a method and apparatus for measuring the surface contour of a test piece which is completely immersed in water or any other liquid which transmits ultrasonic waves.

Ultrasonic techniques have been used in the past for the non-destructive testing of a test piece or the like to determine the presence of flaws therein. These ultrasonic techniques measure the time it takes for an ultrasonic wave to travel from a transducer to the test piece and for the reflected wave to travel back to the transducer. Surface contour measurement using ultrasonics is possible because sound waves are reflected from the surface of the test piece. Thus, when measuring the surface contour of a test piece any surface portion which is curved or somehow misshaped will be detected, because the time necessary for the ultrasonic wave to travel from the transducer to the surface of the test piece and back will change.

One of the types of ultrasonic inspection involves immersion testing where the test piece is completely submerged in a tank containing a liquid, such as water, and acoustically coupled by the fluid to the transducer. The sound waves leave the transducer, travel through the water to the test piece. Echoes are returned to the transducer from the surface of the test piece, and the amount of time it takes the wave to leave and echo back to the transducer is measured.

This measured time is a function of both the distance the wave must travel and the velocity of sound in the medium through which the wave travels. Once the velocity of sound in the medium is known, the distance can be determined accurately by measuring the time of flight with a common oscilloscope or ultrasonic flaw detection equipment. With these ultrasonic techniques, the limiting factor is an accurate measurement of the velocity of sound in the transmitting medium. If the medium between the transducer and the test piece is liquid at a known constant temperature then the velocity of sound in the medium can easily be determined. Once the velocity of sound in the medium is known, the distance between the transducer and the surface of the test piece can also be easily determined.

However, testing a test piece which is at a temperature different from that of the surrounding liquid medium can cause inaccurate measurement. For example, when the surface of the test piece is at a higher temperature than the surrounding liquid, where such liquid is for example water, a path of water with an unknown temperature gradient is created between the transducer and the surface of the test piece. This makes it difficult to accurately determine the temperature of the water over the entire distance from the transducer to the surface of the test piece. Since the velocity of sound in water depends significantly on its temperature, as shown in FIG. 1, and since it is necessary that the changes in of the surface contour be measured within ±0.005 inch, the use of the conventional ultrasonic distance measuring systems, as described above, cannot provide accurate measurements, when testing the surface contour of a test piece having a temperature higher than the temperature of the water in the tank.

Accordingly, the method of the present invention was devised which enables testing the surface of a test piece for its contour (i.e., to determine if it is bowed), which test piece has a surface temperature different from that of the surrounding liquid medium, especially test pieces having a surface at an elevated temperature. Thus, the present invention can be used to measure the surface contour or bow of radioactive fuel rods, etc.

SUMMARY

The present invention is directed to a method and apparatus which provides a system of ultrasonic, non-contact measurement of the surface contour of various test pieces and is particularly applicable when the surface is both under a liquid medium and at a temperature different from the surrounding liquid medium. In the method of the present invention, it is not necessary to know the temperature of the surface of the test piece. Also, in the present invention, it is not necessary to know the temperature of the liquid medium surrounding the test piece. Thus, the present invention provides a great advantage over the conventional ultrasonic measuring systems, because it permits the use of ultrasonic distant measuring techniques for measuring the distance between an ultrasonic transducer and any surface, without any determination of the temperature of the liquid in which the test piece and the transducer are immersed.

In accordance with the present invention, water of a known temperature is introduced between the transducer and the surface of the test piece to be measured. This eliminates problems associated with liquid, for example water, of an unknown temperature gradient being between the transducer and the surface of the test piece.

DESCRIPTION OF THE PREFERRED EMBODIMENTS

Figure 2:
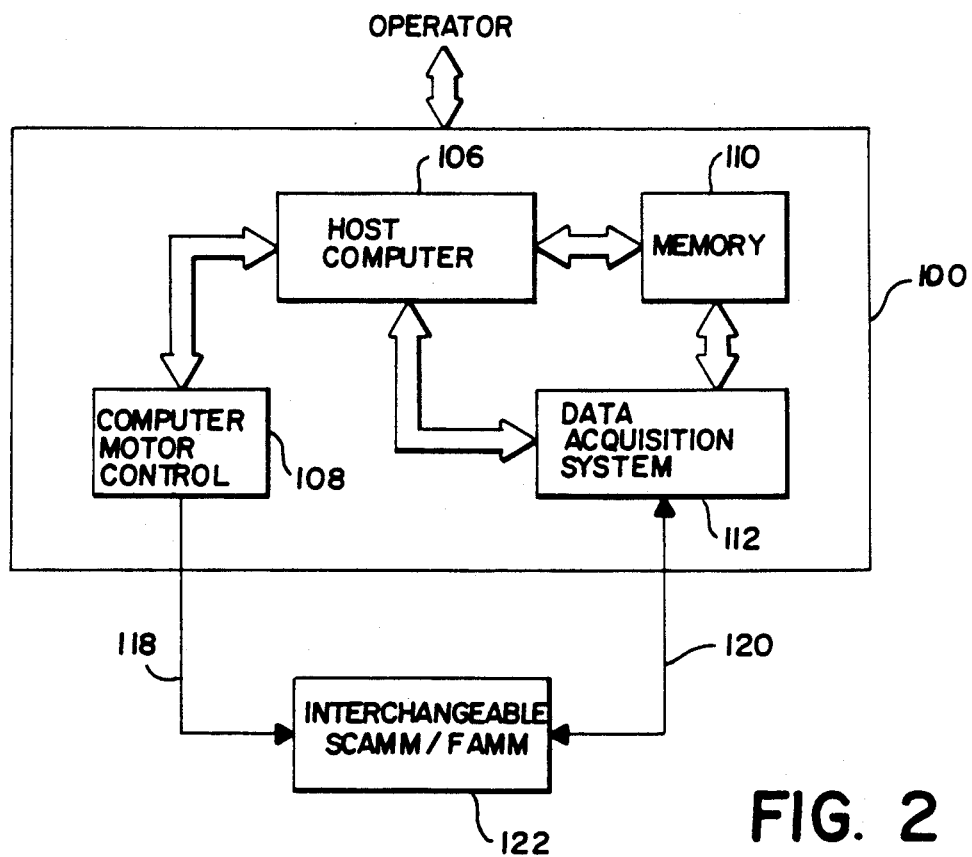
FIG. 2 shows a water system in accordance with the present invention.

FIG. 2 illustrates a water squirter system in accordance with the present invention. In the system shown in FIG. 2, ultrasonic transducer 4 and the test piece 6 are placed within a tank of water (not shown in FIG. 2) and submerged below the surface of the water in the tank. Water at a known and constant temperature is provided from a water source 3 under pressure (i.e., through a water pump) to water input 2 of the measuring device or squirter 10, whereby water is squirted or pushed from measuring device 10 in a column 5 towards the test piece 6, the surface contour of which is to be measured. The ultrasonic transducer 4 is provided within the measuring device 10 and provides ultrasonic waves through the column of water 5 to the surface of the test piece 6. In practice, the water squirter system transmits a column of water of a known, fixed temperature between the transducer and the surface of the test piece. An ultrasonic signal input and signal output system provides an input signal of sufficient power to energize transducer 4 in a conventional manner. The transducer then transmits an ultrasonic wave through the column of water 5 which is reflected by the surface of the test piece and the reflected wave is then received by the transducer. The transducer converts the reflected wave into an electrical signal, namely, the ultrasonic output signal, which is then supplied to an ultrasonic detection instrument to measure the time of flight of the ultrasonic wave. This measured amount of time, along with the velocity of the ultrasonic wave within the water, is used to calculate the distance between the transducer and the surface of the test piece. This distance can be displayed digitally on the ultrasonic equipment, such as the ultrasonic flaw detector having a digital display and screen presentation 8, as shown in FIG. 3.

Figure 3:
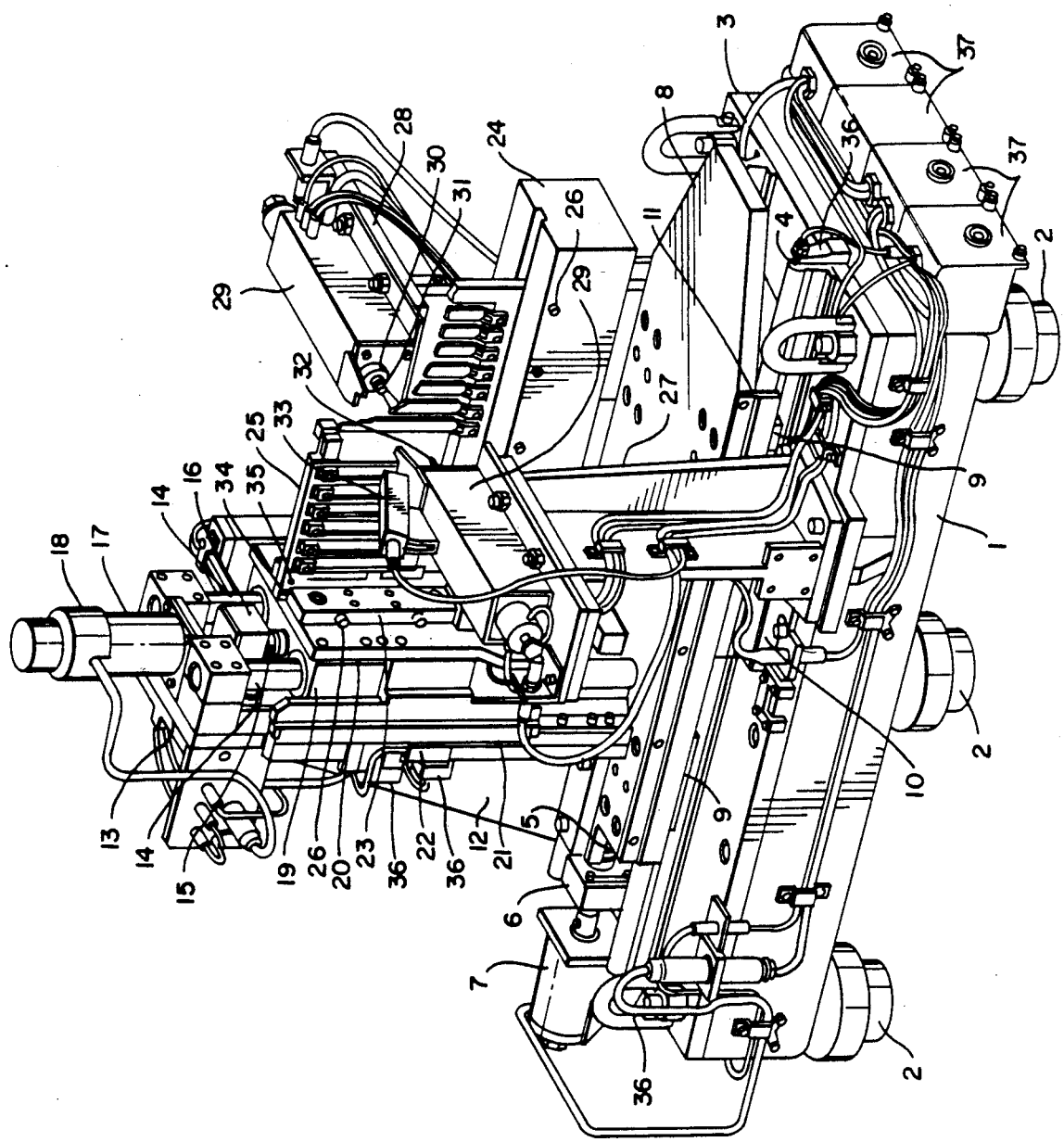
FIG. 3 shows a test system using the present invention.
Figure 3:
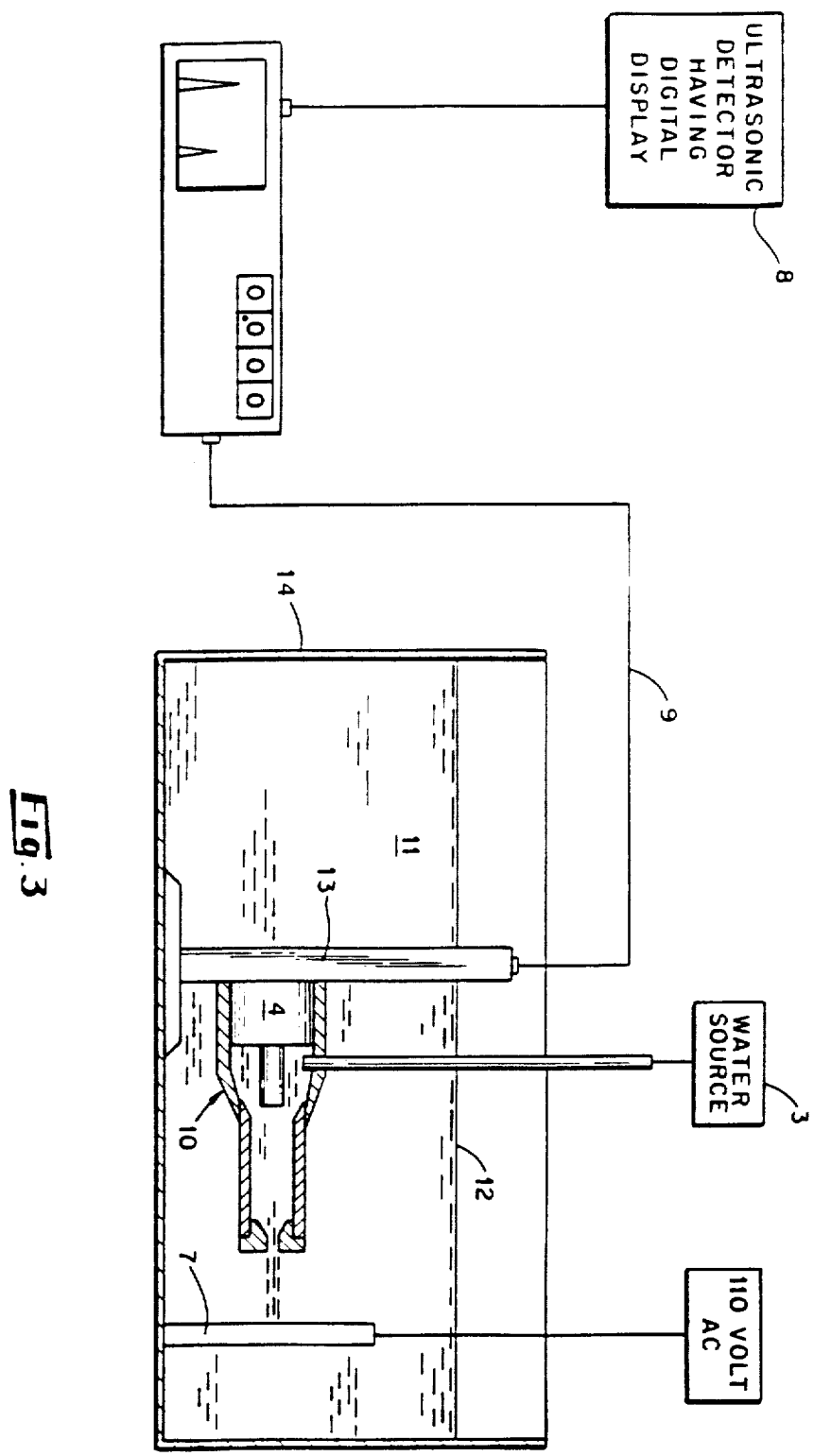
Figure 1:
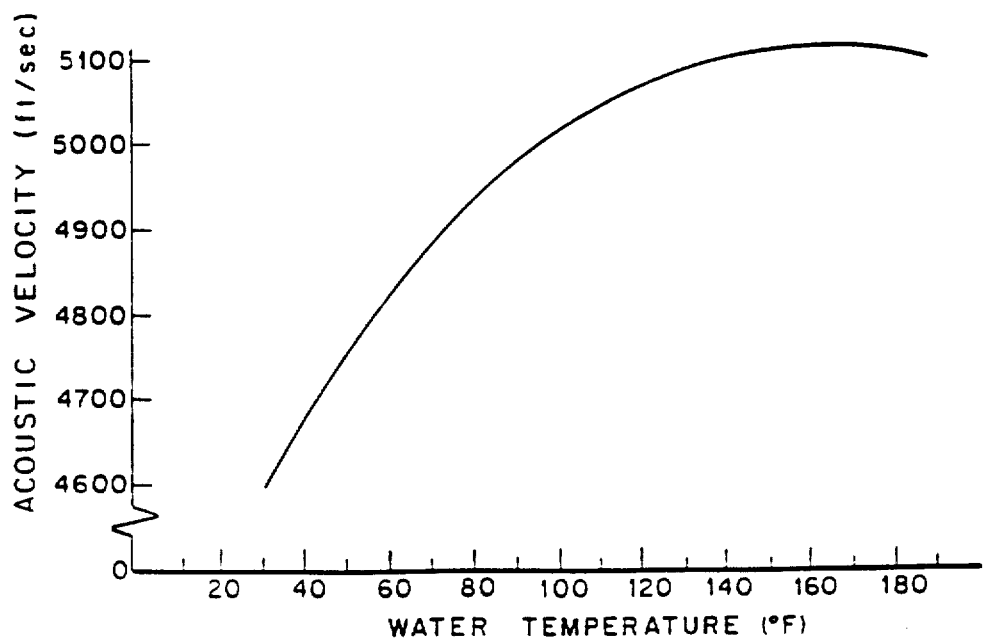
Figure 2:
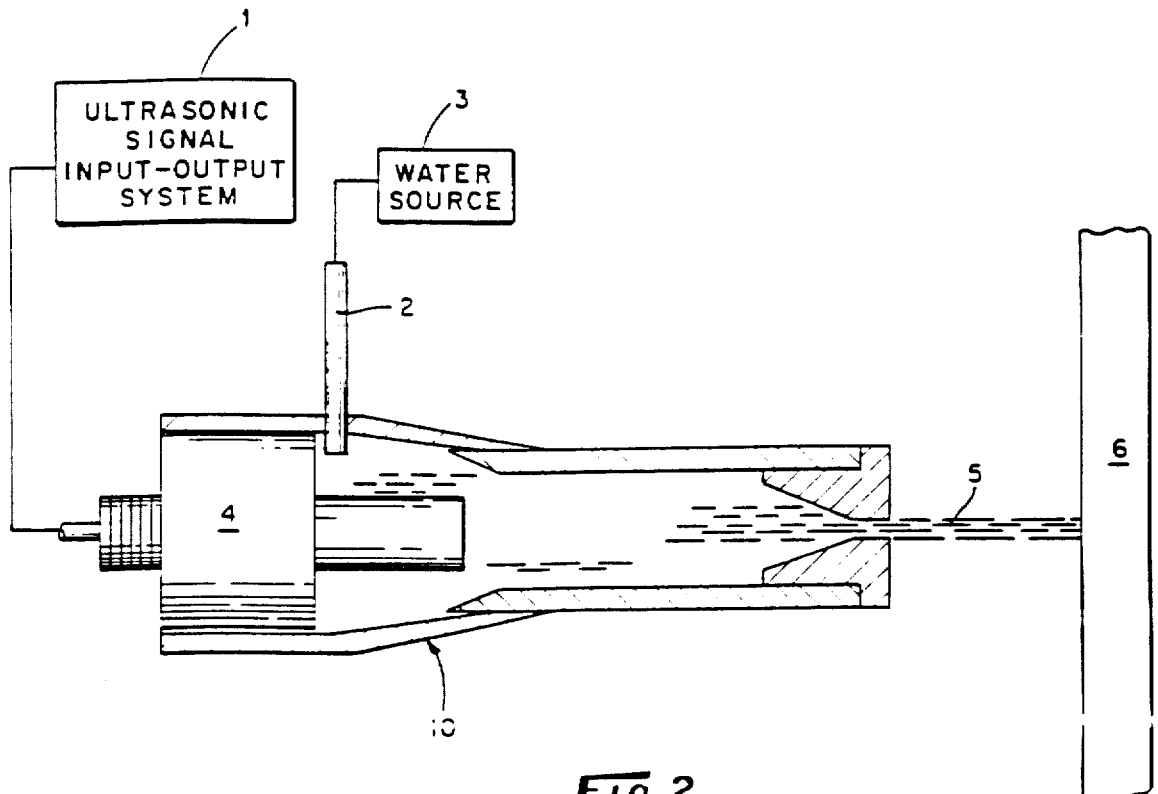

In FIG. 3, the measuring device 10 is arranged on support 13 in a manner which permits the measuring device 10 to move vertically and scan the entire length of the test piece. While not shown, the test piece is supported in the tank so that it is centered and can be rotated to obtain a plurality of measurements at different angles. Wires or other means can be used to support the test piece as is known in the art for this purpose.

The water squirter which is used in the present invention can be a commercially available water squirter which is normally used for transmitting a column of water to any transducer and any surface, while both are surrounded by air. See, for example, U.S. Pat. Nos. 2,751,783 and 4,507,969, respectively of Erdman and Djordjevic et al., which are incorporated herein by reference. The water squirter is designed to transmit a water column of sufficient force to maintain a liquid coupling between the transducer and the test piece because it is important not to transmit the ultrasonic waves through water, the temperature of which is not known. Thus, the distance between the water squirter and the surface of the test piece should be limited to the distance in which the flow force of the squirter is sufficient to provide a column of water between the transducer and the surface of the test piece.

The application for the squirter in this system required it to replace a volume of liquid of an unknown temperature between the transducer and the surface of the test piece with a column of water of known and fixed temperature. See FIG. 2.

The ultrasonic flaw detector can be a commercially available ultrasonic flaw detector, which has commercial modifications which allow it to measure thickness or distance of water between the transducer and the test piece and to display this measurement digitally. It can be a part of or connected to the ultrasonic signal input and signal output system 1, shown in FIG. 2. For convenience. FIG. 3 only shows the ultrasonic flaw detector 8 connected to the transducer 4 via wire g through the support 13. In the system shown in FIG. 3, a Mark II with a Velocity Time Velocity Analog module (made by Staveley NDT Technologies, East Hartford, Conn.), was used for the ultrasonic detector having a digital display and a screen presentation 8. However, other types of ultrasonic flaw detectors can also be used. The detector S in FIG. 3 can produce a voltage which is proportional to the digital display of the measured device. This voltage can then be recorded on a strip chart recorder or similar equipment to produce a record of the surface contour of the test piece being measured.

EXAMPLES

The advantages of the presently claimed invention were demonstrated by use of the test system shown in FIG. 3. The device shown in FIG. 3 is similar to that shown in FIG. 2. An immersion heater 7 was used in place of a radioactive fuel rod to test the ability of the system to accurately measure the distance to a test piece (immersion heater) having a surface temperature higher than that of the water surrounding the test piece, such as a radioactive fuel rod. FIG. 3 also shows water tank 14 filled with water 11 up to surface level 12.

Four different examples were performed. Examples 1 and 2 represent a control group, where all the parts of the system were maintained at ambient temperature.

In examples 3 and 4, the distance to the surface of a heated immersion heater was measured. These examples demonstrate the capabilities of the system, at ambient temperatures, for measuring the surface contour of a test piece at a temperature higher than that of the water in the tank.

EXAMPLE 1

In Example 1, all testing was done with the components including the immersion heater at ambient temperature and no flow of water was provided through the squirter. The observed digital distance reading varied ±0.002 inch over a 30-minute time span.

EXAMPLE 2

Example 2 was conducted in a similar manner to Example 1 except that water was provided through the squirter at ambient temperature. The test results were similar to those Example 1.

EXAMPLE 3

This example was conducted in the same manner as Example 1, except that the immersion heater was turned on at the beginning of the example. As the water in the vicinity of the heater increased in temperature, the digital display changed rapidly until localized boiling occurred on the heater and the ultrasonic waves could no longer be reflected. The change in the digital display was caused by the change in velocity of the ultrasonic waves in the water in the area of the immersion heater. This example demonstrates the phenomena which the present invention overcomes and gave an indication of the error which could be encountered, if the water squirter of the present invention was not used as in the present invention.

EXAMPLE 4

This example demonstrates the advantages of the system of the present invention for measuring surfaces of a test pieces which are at temperatures higher than the surrounding water. In this example, the water squirter was used with water flowing therethrough to the immersion heater, thus creating an acoustical coupling between the transducer and the immersion heater, and the immersion heater was turned on. As the heater caused local heating of the water, the digital display of distance did not vary more than ±0.002 inch, which was the same as that in the control examples, Examples 1 and 2, conducted with all the parts at ambient temperature.

The present invention can be used for measuring the surface properties of a wide variety of test pieces having a wide variety of surface temperatures. In experiments, conducted by the inventors, no temperature range was observed in which the present invention was not effective. Various tests were made on surfaces which caused localized boiling on the surface with no adverse effects. The present system can also be utilized to measure the contour of surfaces with temperatures below that of the ambient water.

We claim:

1. A method for measuring the surface contour of a test piece, which comprises submerging an ultrasonic transducer and a test piece in a liquid medium, flowing a stream of liquid at known and constant temperature between the transducer and the test piece to provide an acoustical coupling therebetween, causing the transducer to transmit ultrasonic waves through said acoustical coupling to the test piece, measuring an amount of time necessary for the waves to travel from the transducer to the test piece and for a reflected wave to be received by the transducer, calculating the distance between the transducer and the test piece based on the measured time of wave travel, and determining the contour of the test piece based thereon.

2. The method of claim 1, wherein the ultrasonic transducer and the test piece are submerged in a tank holding said liquid medium.

3. The method of claim 2, wherein said liquid medium is water.

4. The method of claim 3, wherein said stream of liquid at a known and constant temperature is water.

5. The method of claim 4, wherein the water at a known and constant temperature is provided from outside the tank to a water squirter through a pump.

6. The method of claim 5, wherein the test piece is at a temperature different from that of the water in the tank.

7. The method of claim 6, wherein the test piece is at a temperature higher than that of the water in the tank.

8. The method of claim 1, including calculating said distance by means of an ultrasonic detection instrument with means for receiving a signal from the transducer and digitally displaying said distance between the transducer and the test piece.

9. The method of claim 8, wherein said means for receiving a signal produces a voltage which is proportional to the digital display.

10. The method of claim 9, including means for receiving the voltage and displaying a corresponding recording thereof on a strip chart recorder.

* * * * *

UNITED STATES PATENT AND TRADEMARK OFFICE
CERTIFICATE OF CORRECTION

PATENT NO. : 5,054,321
DATED : October 8, 1991
INVENTOR(S) : Mark S. Horvath, Roy A. Nance, George H. Cohen and George Fodor It is certified that error appears in the above-indentified patent and that said Letters Patent is hereby corrected as shown below:

Title Page should be deleted to appear as per attached Title page.

Figure 1:
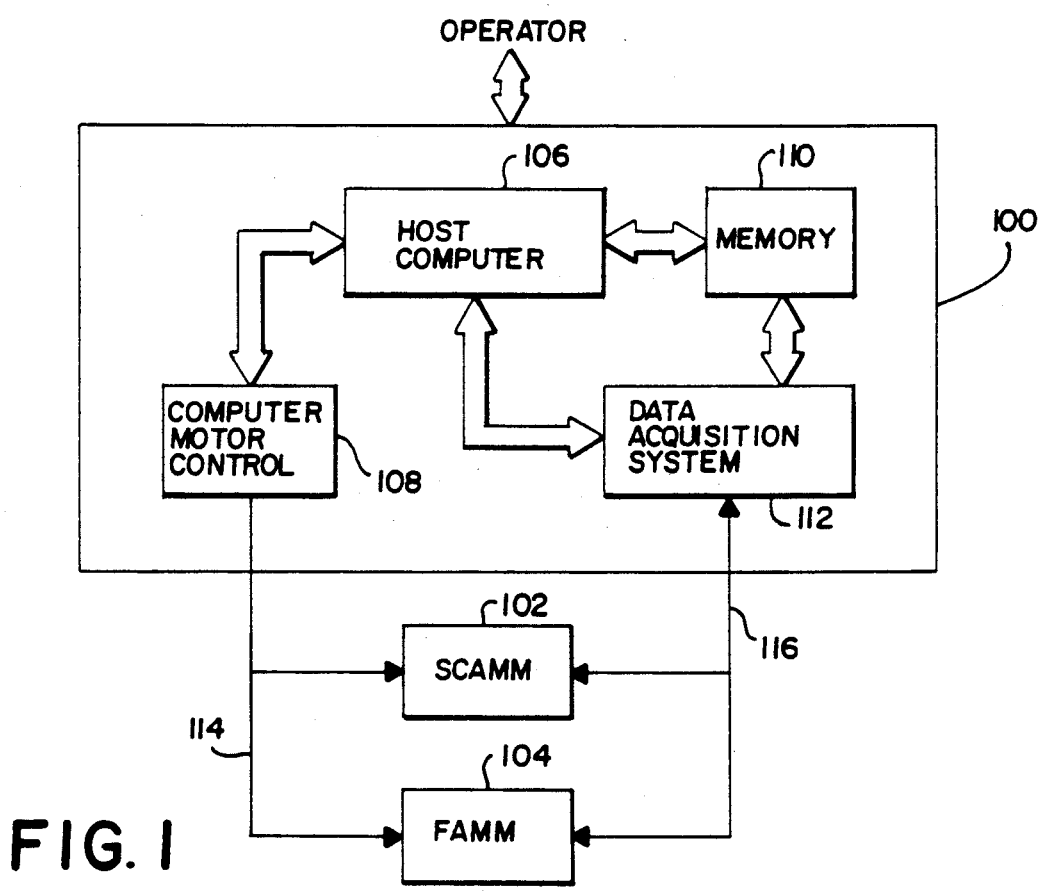
FIG. 1 is graph showing the variation of the acoustical velocity of water versus temperature.

The drawing sheets, consisting of Figs 1, 2 and 3, should be deleted to be replaced with the drawing sheets, consisting of Figs. 1-3, as shown on the attached pages.

Signed and Sealed this

Twenty-eighth Day of December, 1993

Attest:

BRUCE LEHMAN

Attesting Officer

Commissioner of Patents and Trademarks

United States Patent [19]

Horvath et al.

[11] Patent Number: 5,054,321
[45] Date of Patent: Oct. 8, 1991

[54] METHOD AND APPARATUS FOR MEASURING SURFACE CONTOUR ON PARTS WITH ELEVATED TEMPERATURES

[75] Inventors: Mark S. Horvath, Canton, Mich.; Roy A. Nance, McMurray, Pa.; George H. Cohen, Pittsburgh, Pa.; George Fodor, Pittsburgh, Pa.

[73] Assignee: The United States of America as represented by the United States Department of Energy, Washington, D.C.

[21] Appl. No.: 531,356

[22] Filed: May 31, 1990

[51] Int. Cl.⁵ .................................... G01N 29/00
[52] U.S. Cl. ............................. 73/597; 73/644
[58] Field of Search ............ 73/644, 597, 620, 627, 73/629

[56] References Cited

U.S. PATENT DOCUMENTS

| | | | |
|---|---|---|---|
| 2,751,783 | 6/1956 | Erdman | 73/644 |
| 3,662,590 | 5/1972 | Shiraiwa | 73/644 |
| 3,898,839 | 8/1975 | White | 73/644 |
| 3,910,104 | 10/1975 | Davies | 73/644 |
| 3,946,599 | 3/1976 | Patt | 73/644 |
| 4,403,510 | 9/1983 | De Walle | 73/644 |
| 4,483,195 | 11/1984 | Brown et al. | 73/644 |
| 4,507,969 | 4/1985 | Djordjevic | 73/644 |
| 4,526,038 | 7/1985 | Box | 73/644 |
| 4,530,246 | 7/1985 | Pitman | 73/644 |
| 4,558,598 | 12/1985 | Young | 73/644 |
| 4,726,231 | 2/1988 | Tretout et al. | 73/644 |
| 4,862,748 | 9/1989 | Woodmansee | 73/644 |
| 4,944,186 | 7/1990 | Dorr | 73/644 |

Primary Examiner—Hezron E. Williams
Assistant Examiner—Rose M. Finley
Attorney, Agent, or Firm—Virginia B. Caress; William R. Moser; Richard E. Constant

[57] ABSTRACT

The invention is directed to a method and apparatus for measuring the surface contour of a test piece, such as the bow of a radioactive fuel rod, which is completely immersed in water. The invention utilizes ultrasonic technology and is capable of measuring surface contours of test pieces which are at a higher temperature than the surrounding water. The presence of a test piece at a higher temperature adversely affects the distance measurements by causing thermal variations in the water near the surface of the test piece. The contour measurements depend upon a constant temperature of the water in the path of the ultrasonic wave to provide a constant acoustical velocity (the measurement is made by the time of flight measurement for an ultrasonic wave). Therefore, any variations of water temperature near the surface will introduce errors degrading the measurement. The present invention overcomes these problems by assuring that the supply of water through which the ultrasonic waves travel is at a predetermined and constant temperature.

10 Claims, 2 Drawing Sheets

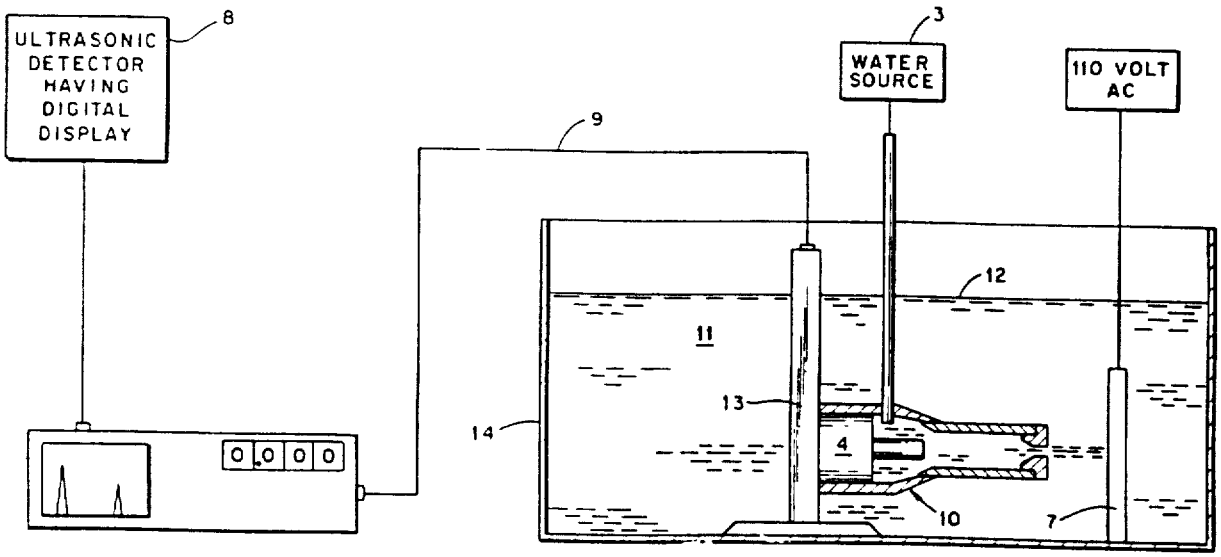

Fig. 3